US008158345B2

(12) United States Patent
Bernal-Mendez et al.

(10) Patent No.: US 8,158,345 B2
(45) Date of Patent: Apr. 17, 2012

(54) LABELED OLIGONUCLEOTIDE

(75) Inventors: Eloy Bernal-Mendez, Saint-Quentin-Fallavier (FR); Ali Laayoun, Colombe (FR); Alain Laurent, Grenoble (FR)

(73) Assignee: Biomerieux, Marcy l'Etoile (FR)

( * ) Notice: Subject to any disclaimer, the term of this patent is extended or adjusted under 35 U.S.C. 154(b) by 39 days.

(21) Appl. No.: 12/310,556

(22) PCT Filed: Sep. 26, 2007

(86) PCT No.: PCT/FR2007/052007
§ 371 (c)(1),
(2), (4) Date: Feb. 27, 2009

(87) PCT Pub. No.: WO2008/037924
PCT Pub. Date: Apr. 3, 2008

(65) Prior Publication Data
US 2009/0311688 A1 Dec. 17, 2009

(30) Foreign Application Priority Data
Sep. 28, 2006 (FR) ..................... 06 53982

(51) Int. Cl.
*C12Q 1/68* (2006.01)
*C07H 21/02* (2006.01)
*C07H 21/04* (2006.01)
(52) U.S. Cl. .................. 435/6; 536/23.1; 536/24.3
(58) Field of Classification Search ..... 435/6; 536/23.1, 536/24.3
See application file for complete search history.

(56) References Cited

U.S. PATENT DOCUMENTS

| 5,866,336 | A | | 2/1999 | Nazarenko et al. | |
|---|---|---|---|---|---|
| 6,037,130 | A | * | 3/2000 | Tyagi et al. | 435/6 |
| 6,117,635 | A | | 9/2000 | Nazarenko et al. | |
| 8,067,165 | B2 | * | 11/2011 | Livak et al. | 435/91.1 |
| 2003/0134307 | A1 | * | 7/2003 | Beckman et al. | 435/6 |
| 2005/0059049 | A1 | | 3/2005 | Moen et al. | |
| 2009/0104614 | A1 | * | 4/2009 | Tsourkas et al. | 435/6 |
| 2009/0280477 | A1 | | 11/2009 | Coull et al. | |

FOREIGN PATENT DOCUMENTS

| EP | 0 569 272 A1 | 11/1993 |
|---|---|---|
| WO | WO 88/04301 | 6/1988 |
| WO | WO 90/15813 | 12/1990 |
| WO | WO 95/13399 | 5/1995 |
| WO | WO 96/19240 A1 | 6/1996 |
| WO | WO 00/32810 | 6/2000 |
| WO | WO 2007/114986 A2 | 10/2007 |

OTHER PUBLICATIONS

Morvan et al., Nucleic Acids Research 16 (3) : 833-847 (1988).*
Hirose et al. Nucleic Acids Research Supplement 2 :263-264 (2002).*
Belanger et al.,Rapid Detection of Shiga Toxin-Producing Bacteria in Feces by Multiplex PCR with Molecular Beacons on the Smart Cycler. J.of Clinical Microbiology 40(4) :1436 (2002).*
Ishchenko et al., Uncoupling of the base excision and nucleotide incision repair pathways reveals their respective biological roles. PNAS 103(8) : 2564 (Feb. 2006).*
Araminio et al., Solution Structure of a DNA Duplex Containing an α-Anomeric Adenosine: Insights into Substrate Recognition by Endonuclease IV. J. of Molecular Biology 338 :77-91 (2004).*
Vichier-Guerre et al., New Insights into the Resistance of α-Oligonucleotides to Nucleases. Antisense Research and Development 4 : 9-18 (1994).*
Cazenave et al. Rate of degradation of [α]-and [β]oligodeoxynucleotides in *Xenopus oocytes*. Implications for anti-messenger strategies. Nucleic Acids Res. 15: 10507-10521 (1987).*
Tyagi, Sanjay et al., "Molecular Beacons: Probes that Fluoresce upon Hybridization", Nature Biotechnology, Mar. 1996, pp. 303-308, vol. 14, Department of Molecular Genetics, Public Health Research Institute, New York, NY.
Jun. 16, 2008 International Search Report issued in PCT/FR2007/052007 (with Translation).
Yi et al., "Molecular Zipper: A Fluorescent Probe for Real-Time Isothermal DNA Amplification," Nucleic Acids Research, Oxford University Press, vol. 34, No. 11, 2006, pp. 1-5.
Zhang et al., "Detection of Target Nucleic Acids and Proteins by Amplification of Circularizable Probes," Expert Review of Molecular Diagnostics, Future Drugs, London, GB, vol. 3, No. 2, 2003, pp. 237-248.
Zhang et al., "Amplification of Circularizable Probes for the Detection of Target Nucleic Acids and Proteins," Clinica Chimica Acta, Elsevier, BV, Amsterdam, vol. 363, No. 1-2, 2006, pp. 61-70.
Weusten et al., "Principles of Quantitation of Viral Loads Using Nucleic Acid Sequence-Based Amplification in Combination With Homogeneous Detection Using Molecular Beacons," Nucleic Acids Research, 2002, Oxford University Press, vol. 30, No. 6, pp. 1-7.
Koga et al., "Alternating α,β-Oligothymidylates with Alternating (3'→3')- and (5'→5')-Internucleotidic Phosphodiester Linkages as Models for Antisense Oligodeoxyribonucleotides," The Journal of Organic Chemistry, vol. 56, No. 12, Jun. 7, 1991, pp. 3757-3759.
Tsourkas et al., "Structure-Function Relationships of Shared-Stem and Conventional Molecular Beacons," Nucleic Acids Research, Oxford University Press, Oct. 2002, vol. 30, No. 19, pp. 4208-4215.
Browne, "Sequence-Specific, Self-Reporting Hairpin Inversion Probes," J. Am. Chem. Soc. 2005, vol. 127, pp. 1989-1994.
Crey-Desbiolles et al., "Molecular Beacons With a Homo-DNA Stem: Improving Target Selectivity," Nucleic Acids Research, 2005, vol. 33, No. 8, pp. 1-7.
Co-pending U.S. Appl. No. 12/225,693, filed Sep. 26, 2008, Eloy Bernal Mendez et al.
Co-pending U.S. Appl. No. 12/926,962, filed Dec. 20, 2010, Eloy Bernal Mendez et al.
Co-pending U.S Appl. No. 12/996,457, filed Dec. 6, 2010, Ali Laayoun et al.

(Continued)

Primary Examiner — Ethan C Whisenant

(57) ABSTRACT

The present invention relates to a labeled oligonucleotide comprising a first nucleotide segment and a second nucleotide segment, complementary to a target sequence, a fluorophore, a quencher and at least one alpha-anomeric nucleoside. The invention also relates to the use of such an oligonucleotide and also to a process using such an oligonucleotide.

19 Claims, 9 Drawing Sheets

OTHER PUBLICATIONS

Jan. 7, 2010 Office Action issued in U.S. Appl. No. 12/225,693.
Aug. 19, 2010 Office Action issued in U.S. Appl. No. 12/225,693.
Mar. 5, 2010 Office Action issued in U.S. Appl. No. 12/225,693.
Shchepinov et al., "Oligonucleotide Dendrimers: Synthesis and Use as Polylabelled DNA Probes," Nucelic Acids Research, vol. 25, No. 22, pp. 4447-4454, 1997.
Afonina et al., "Minor Groove Binder-Conjugated DNA Probes for Quantitative DNA Detection by Hybridization-Triggered Fluorescence," Biotechniques, vol. 32, No. 4, pp. 940-949, 2002.
Feb. 14, 2008 International Search Report issued in PCT/FR2007/051159.
Striebel et al., "Enhancing Sensitivity of Human Herpes Virus Diagnosis with DNA Microarrays Using Dendrimers," Experimental and Molecular Pathology, vol. 77, 2004, pp. 89-97.
Dec. 7, 2011 Restriction Requirement issued in U.S. Appl. No. 12/996,457.
Jan. 10, 2012 Office Action issued in U.S. Appl. No. 12/926,962.
Feb. 10, 2012 Office Action issued in U.S. Appl. No. 12/996,457.

\* cited by examiner

LABELED OLIGONUCLEOTIDE

The present invention relates to a novel labeled oligonucleotide. The invention also relates to the use of such an oligonucleotide and also to a method using such an oligonucleotide.

In technologies relating to nucleic acids and to genetic material, it is often necessary to determine whether a gene, a part of a gene or a nucleotide sequence is present in a living organism, a cell extract of this organism or any other biological sample.

Various types of methods for detecting nucleic acids are described in the literature. These methods, and particularly those which require the detection of polynucleotides, are based on the pairing properties of the complementary strands of nucleic acids, commonly termed "nucleic acid hybridization" or simply "hybridization".

In general, after having identified the specific sequence of an organism or of a disease which should be analyzed, it is advisable to extract the nucleic acids of a sample, and to amplify and detect the sequence of interest. Many amplification and detection methods have been developed for this purpose.

Thus, PCR (polymerase chain reaction) is based on the repetition of a three-stage process: denaturation of the double-stranded DNA, hybridization of the primers to the single-stranded DNA, and enzymatic extension of the primers with a thermostable DNA polymerase, which synthesizes a DNA strand complementary to that acting as a target for the oligonucleotide primers.

The amplification can be analyzed at the end point of the cycle (end point PCR) or in real time (real time PCR) through the use of fluorescent labeling of the amplified product. Several real time PCR techniques exist. One of them uses particular probes called "molecular beacons", which are hairpin sequences comprising a loop structure and a stem containing a fluorophore at one end of the sequence and a quencher at the other (Tyagi, S. and Kramer, F D., Nat. Biotechnol., 1996, 14, 303-308, Marras, S A. et al., Genet Anal., 1999, 14, 151-156). Below the hybridization temperature, these sequences, not hybridized to a target sequence, adopt a "hairpin" configuration: the 5' and 3' ends are close, there is no emission of fluorescence. When the probe, via the loop sequence, recognizes and hybridizes to an amplicon, which corresponds to the amplified target sequence, the stem structure is destabilized, the ends are far apart, the quencher no longer plays its role and there is emission of fluorescence.

However, under certain conditions, the emission of fluorescence by "molecular beacon" probes may be "parasitized" by a background noise due to the fluorophore and the quencher being moved apart following degradation by nucleases present during the amplification reaction. This is in particular the case of a "conventional" PCR, since the Taq polymerase enzyme itself has 5'-nuclease activity. Furthermore, in addition to the "parasitic" fluorescence emission which appears during a real time PCR, cleaving of the molecular beacons due to the residual presence of a thermostable polymerase enzyme at the end of the cycle affects a post-amplification end-point temperature gradient analysis. Now, this post-amplification end-point temperature gradient analysis is the most sensitive method for detecting simple sequence variations, such as SNPs (single nucleotide polymorphisms) using molecular beacons.

NASBA is another isothermal nucleic acid amplification technology, which is based on the joint action of three enzymes (AMV reverse transcriptase, RNAse-H and T7 RNA polymerase). The amplification can be analyzed at the end of the cycle (end point NASBA) or in real time (real time NASBA) through the use of fluorescent labeling of the amplified product, using molecular beacon probes. However, in end point, the presence of RNAse H, an essential enzyme during the initiation of NASBA, can, at the end of the reaction, induce degradation of the target RNA hybridized on the molecular beacon. A decrease in the fluorescence signal which is due to the cleavage of the target RNA is then observed. An amplification end-point temperature-gradient analysis is therefore difficult.

Whether in PCR or in NASBA, the fluorescence emission may also be parasitized through the nonspecific hybridization of the stem part of the molecular beacon on the amplicon. It is then important to reduce this parasitic hybridization.

Finally, molecular beacons may also be used for the detection of target sequences independently of an amplification. In fact, it is possible to analyze the expression of a gene in living cells by means of the injection of molecular beacons, the fluorescence emitted reflecting the hybridization of the probe on a target transcript. However, the presence of numerous nucleases undergoing activity in the cell implies extensive degradation of the probes, and therefore induces the emission of fluorescence, which is not due to the hybridization of the probe on a target sequence.

It is therefore important to improve the current amplification techniques in order to make them more sensitive, by decreasing in particular the phenomena of cleavage and of nonspecific hybridization of the molecular beacons of the prior art.

The present invention proposes to solve all the drawbacks of the prior art by providing novel labeled oligonucleotides, which are specific, stable and resistant to nucleases.

In this respect, the invention relates to a labeled oligonucleotide comprising a first nucleotide segment, a second nucleotide segment, complementary to a target sequence, and a third nucleotide segment, complementary to said first nucleotide segment, characterized in that it comprises a fluorophore, a quencher and at least one alpha-anomeric nucleoside.

Preferably, said first and third segments are on either side of the second segment.

Preferably, the labeled oligonucleotide according to the invention is characterized in that said second segment comprises at least one alpha-anomeric nucleoside.

Preferably, said second segment comprises at least 5, at least 10, at least 15, at least 20, at least 25 alpha-anomeric nucleosides.

Preferably, said second segment consists of alpha-anomeric nucleosides.

Preferably, the labeled oligonucleotide according to the invention is characterized in that the fluorophore is at one end of said oligonucleotide and the quencher is at the other end of said oligonucleotide.

Preferably, said fluorophore is a fluorescein. Preferably, said quencher is dabsyl.

Preferably, said first segment comprises from 3 to 8 nucleotides, said second segment comprises from 10 to 35 nucleotides, and said third segment, when it is present, comprises from 3 to 8 nucleotides.

The invention also relates to the use of an oligonucleotide comprising at least one alpha-anomeric nucleoside, for blocking a 5' nuclease activity of a polymerase enzyme and/or for blocking an RNAseH activity. Such uses are very relevant since it is thus possible to detect a target sequence by using probes of molecular beacon type while at the same time avoiding the cleavage thereof by the 5' nuclease activity of a polymerase enzyme during a polymerase chain reaction or during post-amplification end-point measurements, or by the nuclease activity of an RNAse H, in particular in NASBA, during end-point measurements.

The invention also relates to a method for detecting a nucleic material in a biological sample, comprising the following steps:
a) extracting the nucleic material from a biological sample,
b) amplifying the nucleic material in order to obtain amplicons of at least one target sequence of the nucleic material;
c) using, simultaneously with step b) or subsequent to step b), at least one labeled oligonucleotide according to the invention;
d) detecting the presence of said amplicons.

According to one preferred embodiment of the invention, the nucleic material is amplified by PCR.

According to another preferred embodiment of the invention, the nucleic material is amplified by NASBA.

The following definitions will make it possible to understand the invention more clearly.

For the purpose of the present invention, the term "upstream" is intended to mean a region located on the 5'-end side of the nucleic acid or of the polynucleotide sequence, and the term "downstream" is intended to mean a region located on the 3'-end side of said nucleic acid or of said polynucleotide region.

The terms "nucleotide fragment", "nucleic acid fragments", "nucleotide segment", "nucleic acid segment", "nucleotide sequence", "nucleic acid sequence", or "oligonucleotide" denote a natural DNA or RNA fragment, a natural or synthetic polynucleotide, a synthetic DNA or RNA fragment which is unmodified or which comprises at least one modified base such as inosine, methyl-5-deoxycitidine, dimethylamino-5-deoxyuridine, deoxyuridine, diamino-2,6-purine, bromo-5-deoxyuridine, pseudouridine or pseudoisocytidine, or any other modified base, which allows hybridization. Each of the modifications may be taken in combination.

The term "labeled oligonucleotide" or "probe" is intended to mean a series of nucleosides, also comprising at least one molecule for detecting said oligonucleotide.

This oligonucleotide may in particular be a detection probe, which acts by molecular recognition. The expression "detection probe which acts by molecular recognition" is intended to mean a nucleic sequence of 10 to 100 nucleotide units, in particular of 15 to 45 nucleotide units, which has a hybridization specificity under given conditions so as to form a hybridization complex with a target nucleic acid, and which emits a signal when the probe hybridizes to the target nucleic sequence.

The detection probe may in particular be a molecular beacon detection probe as described by Tyagi & Kramer (Nature Biotech, 1996, 14: 303-308). These molecular beacons become fluorescent during hybridization. They have a stem-loop structure and contain a fluorophore and a quencher group. The binding of the specific loop sequence with its complementary target nucleic acid sequence causes the stem to unfold and a fluorescent signal to be emitted during excitation at the appropriate wavelength.

The detection probe may in particular be a probe integrated into primers of the "Scorpion®" (Nucleic Acids Research, 2000, Vol. 28, No. 19 3752-3761) or "Amplifluor®" (Genome Research Vol 1 163-169, 2001 Myakishev M. et al) type.

Amplifluors® are nucleotide sequences, which have, on the 5' side, a sequence with a stem-root structure, with a fluorophore at the 5' end and a Dabsyl-type quencher at the other end of the structure. On the 3' side, Amplifluors® have a sequence, which is complementary to a sequence of the target and which acts as a primer during the amplification reaction.

Scorpions® are sequences, which have, on the 5' side, a sequence with a stem-loop structure with a quencher at one end of said structure and a fluorophore at the other end of said structure. On the 3' side, Scorpions® have a sequence, which is complementary to a sequence of the target and which acts as a primer during the amplification reaction. In the conventional Scorpion mode, a "spacer", located between the primer sequence and the stem-loop sequence, makes it possible to prevent recognition of the stem-loop sequence by the polymerase. This spacer becomes optional if the Scorpions are produced according to the invention.

For the purpose of the present invention, the term "fluorophore" is intended to mean a molecule, which emits a fluorescence signal between 500 and 700 nm when it is excited by light at a wavelength which is suitable (or between 450 and 650 nm). The fluorophore may in particular be a rhodamine or a derivative such as Texas Red, a fluorescein or a derivative, such as 5-bromomethylfluorescein, a fluorophore of the Alexa family, such as Alexa532, Alexa647, Alexa 405, Alexa 700 or Alexa 680, or any other fluorophore which is suitable according to the measuring device used. The available fluorophores for the detection probes are very varied and known to those skilled in the art.

For the purpose of the present invention, the term "fluorescein" is intended to mean an aromatic chemical molecule which emits a fluorescence signal with a maximum emission around 530 nm, when it is excited by light at a wavelength of around 495 nm.

For the purpose of the present invention, the term "quencher" is intended to mean a molecule, which interferes with the fluorescence emitted by a fluorophore. This quencher is in particular chosen from aromatic molecules, which are nonfluorescent, so as to avoid parasitic emissions. Preferably, said "quencher" is a Dabsyl or a Dabcyl or a "Black hole Quencher™". Dabcyl, Dabsyl and the "Black hole Quenchers™" are nonfluorescent aromatic molecules, which prevent the emission of fluorescence when they are physically in proximity to a fluorophore, or by FRET.

The term "alpha-anomeric nucleoside" or "alpha-nucleosides" or "nucleosides alpha" is intended to mean deoxynucleosides with an unnatural alpha-anomeric configuration, in which the nitrogenous base borne by the anomeric carbon of the deoxyribose is located below the plane instead of being above the plane, as in the case of beta-nucleosides. Preferably, the alpha-nucleotides are those described in application WO 88/04301.

The term "end" is intended to mean the starting point or the terminating point of the synthesis of an oligonucleotide generally defined by the number carried by the free hydroxyls borne by the first or the last nucleoside, i.e. 3' or 5'. It is understood that, through an appropriate choice of the elongation units (alpha- or beta-nucleoside phosphoramidites), an oligonucleotide can be synthesized in the 3' to 5' direction or vice versa, or the direction of elongation can even be alternated during the synthesis. This results in oligonucleotides bearing 3'-5',5'-3' or 3'-3',5'-5' ends.

The term "first segment" is intended to mean a nucleotide sequence, which may be complementary to and have a polarity suitable for said third segment when the latter is present.

The term "second segment" is intended to mean a nucleotide sequence, which is complementary to and has a polarity suitable for the sequence of the target.

The term "third segment" is intended to mean a nucleotide sequence, which is complementary to and has a polarity suitable for said first segment.

The term "stem" parts is also used for said first and third segments, and the term "loop" part is also used for said second segment. This particular embodiment makes it possible to obtain a labeled oligonucleotide of molecular beacon type.

The expression "sequence or region capable of hybridizing on another sequence/region, or complementary sequence" is intended to mean a sequence or a region that can hybridize on another sequence/region under hybridization conditions, which can be determined in each case in a known manner. Reference is also made to complementary sequences/regions. A sequence or region, which is strictly complementary to another, is a sequence in which each of the bases can pair with a base of the other sequence, without mismatching. The term "hybridization" is intended to mean the process during which, under suitable conditions, two nucleotide fragments, having sufficiently complementary sequences, are capable of forming a double strand with stable and specific hydrogen bonds. The hybridization conditions are determined by the stringency, i.e. the strictness of the working conditions. The higher the stringency at which the hybridization is carried out, the more specific it is. The stringency is defined in particular as a function of the base composition of a probe/target duplex, and also by the degree of mismatching between two nucleic acids. The stringency can also depend on the reaction parameters, such as the concentration and the type of ionic species present in the hybridization solution, the nature and the concentration of denaturing agents and/or the hybridization temperature. The stringency of the conditions under which a hybridization reaction should be carried out will depend mainly on the hybridization probes used. All these data are well known to those skilled in the art and the appropriate conditions can be determined by those skilled in the art.

The term "polarity" is intended to mean the orientation of the nucleotide sequence, 5' to 3' or 3' to 5', relative to its complementary sequence. Thus, segments may be oriented in:
- antiparallel fashion: this is the case of an oligonucleotide of natural β-configuration and of its target of natural β-configuration, or it is the case of an oligonucleotide of unnatural α-configuration and of its target of unnatural α-configuration;
- parallel fashion: this is the case of an oligonucleotide of unnatural α-configuration and of its target of natural β-configuration. According to these polarity rules, it is possible to obtain 5'-3', 3'-3' or 5'-5' oligonucleotides, which are synthesized by those skilled in the art from suitable molecules.

The term "polymerase enzyme" is intended to mean an enzyme capable of synthesizing a complementary DNA or RNA fragment from a nucleic acid template and using an initiating oligonucleotide (or primer). Polymerase enzymes sometimes have a nuclease activity, which results in degradation of the nucleic acid fragments, which hybridize on the target being copied: blocking this activity is then highly relevant in a real-time approach since the signal recorded is due only to the molecular recognition and not to enzymatic degradation.

For the purpose of the present invention, the term "nucleic material" is intended to mean a nucleic acid sequence such as a deoxyribonucleic acid (DNA) or ribonucleic acid (RNA) sequence. According to one preferred embodiment of the invention, the nucleic material comprises a deoxyribonucleic acid sequence. According to one preferred embodiment of the invention, the nucleic material is extracted from a biological sample taken from a patient.

For the purpose of the present invention, the term "biological sample" is intended to mean any sample that may contain a nucleic material as defined hereinafter. This biological sample may be taken from a patient and may in particular be a tissue sample, blood sample, serum sample, saliva sample or sample of circulating cells from the patient. This sample may also be a food sample. This biological sample is provided by any means of taking a sample known to those skilled in the art.

For the purpose of the present invention, the term "target sequence" is intended to mean a nucleotide sequence of which at least one part of the series of nucleotide units is specific for and complementary to the nucleotide sequence of the detection probe used.

For the purpose of the present invention, during step a), the nucleic material is extracted from a biological sample by any protocol known to those skilled in the art. By way of indication, the extraction of nucleic acids can be carried out by means of a step of lysis of the cells present in the biological sample, in order to release the nucleic acids contained in the protein and/or lipid envelopes of the cells (such as cell debris which disturbs the subsequent reactions). By way of example, the lysis methods as described in patent applications WO 00/05338 relating to mixed magnetic and mechanical lysis, WO 99/53304 relating to electrical lysis, and WO 99/15321 relating to mechanical lysis, may be used.

Those skilled in the art may use other, well-known lysis methods, such as heat shock or osmotic shock or chemical lyses with chaotropic agents such as guanidium salts (U.S. Pat. No. 5,234,809). This lysis step may also be followed by a purification step, for separating the nucleic acids from the other cell constituents released in the lysis step. This step generally makes it possible to concentrate the nucleic acids, and can be adapted to the purification of DNA or of RNA. By way of example, it is possible to use magnetic particles optionally coated with oligonucleotides, by adsorption or covalence (in this respect, see U.S. Pat. No. 4,672,040 and U.S. Pat. No. 5,750,338), and thus to purify the nucleic acids which have bound to these magnetic particles, by means of a washing step. This nucleic acid purification step is particularly advantageous if it is desired to subsequently amplify said nucleic acids. A particularly advantageous embodiment of these magnetic particles is described in patent applications WO 97/45202 and WO 99/35500. Another advantageous example of a method for purifying nucleic acids is the use of silica, either in the form of a column, or in the form of inert particles (Boom R. et al., J. Clin. Microbiol., 1990, no. 28(3), p. 495-503) or magnetic particles (Merck: MagPrep® Silica, Promega: MagneSil™ Paramagnetic particles). Other very widely used methods are based on ion exchange resins in a column or in a paramagnetic particulate format (Whatman: DEAE-Agarose) (Levison PR et al., J. Chromatography, 1998, p. 337-344). Another method, which is very relevant but not exclusive for the invention is, that of adsorption onto a metal oxide carrier (the company Xtrana: Xtra-Bind™ matrix).

When it is desired to specifically extract the DNA from a biological sample, an extraction with phenol, chloroform and alcohol can be carried out in order to eliminate the proteins, and the DNA can be precipitated with 70% alcohol. The DNA can then be pelletted by centrifugation, washed and resuspended.

For the purpose of the present invention, "step b)" is a process generating multiple copies (or amplicons) of a nucleic sequence by means of the action of at least one polymerase enzyme. For the purpose of the present invention, the term "amplicons" is intended to mean the copies of the target sequence that are obtained during an enzymatic amplification reaction.

According to one preferred embodiment of the invention, the nucleic material is amplified by PCR and step b) is a succession of cycles comprising the following steps:

denaturation of the target sequence in order to obtain two complementary target DNA strands, or to destructure the target RNA strand, hybridization of each of the target strands, obtained during the preceding denaturation step, with at least one amplification primer, formation, from the amplification primers, of the strands complementary to the strands to which they are hybridized, in the presence of a polymerase enzyme and of nucleoside triphosphates, this cycle being repeated a given number of times in order to obtain the target sequence in a sufficient concentration to allow its detection.

According to this embodiment, steps b) and c) are carried out at the same time or one after the other.

When steps b) and c) are carried out at the same time, this embodiment is preferably implemented by "real time PCR", which combines the PCR amplification technique and the detection in a single step, and which makes use in particular of molecular beacons. The PCR reaction takes place in the tube, producing amplicons with which the specific molecular beacons can hybridize so as to give a fluorescent signal. The formation of the new DNA molecules is measured in real time by verifying the signal in a fluorescent reader, during the hybridization step. The use of labeled oligonucleotides according to the present invention makes it possible to avoid the detection probes being degraded by the amplification enzyme (for example, Taq polymerase), thereby increasing the sensitivity of the detection and improving the effectiveness of the technique.

When steps b) and c) are carried out one after the other, the PCR reaction takes place in the tube, producing amplicons. At the end of this amplification step, the molecular beacons are added to the reaction medium, and can hybridize so as to give a fluorescent signal. The use of labeled oligonucleotides according to the present invention makes it possible to avoid the detection probes being degraded by the thermostable polymerase amplification enzyme, which remains residually in the reaction tube, thereby increasing the sensitivity of the detection and improving the effectiveness of the technique.

According to another preferred embodiment of the invention, during step b), the nucleic material is amplified by NASBA.

According to this embodiment, steps b) and c) are preferably carried out one after the other. At the end of the amplification step, the molecular beacons are added to the reaction medium, and can hybridize so as to give a fluorescent signal. The use of labeled oligonucleotides according to the present invention makes it possible to avoid the detection probes being degraded by the RNAse H enzyme, which remains residually in the reaction tube, thereby increasing the sensitivity of the detection and improving the effectiveness of the technique.

"Step d)" is performed by detecting the fluorescence signal emitted during the hybridization of the labeled oligonucleotide according to the invention on the amplicon, and can be carried out by any of the protocols known to those skilled in the art.

The attached figures are given by way of explanatory example and are in no way limiting in nature. They will make it possible to understand the invention more clearly.

Figure 1:
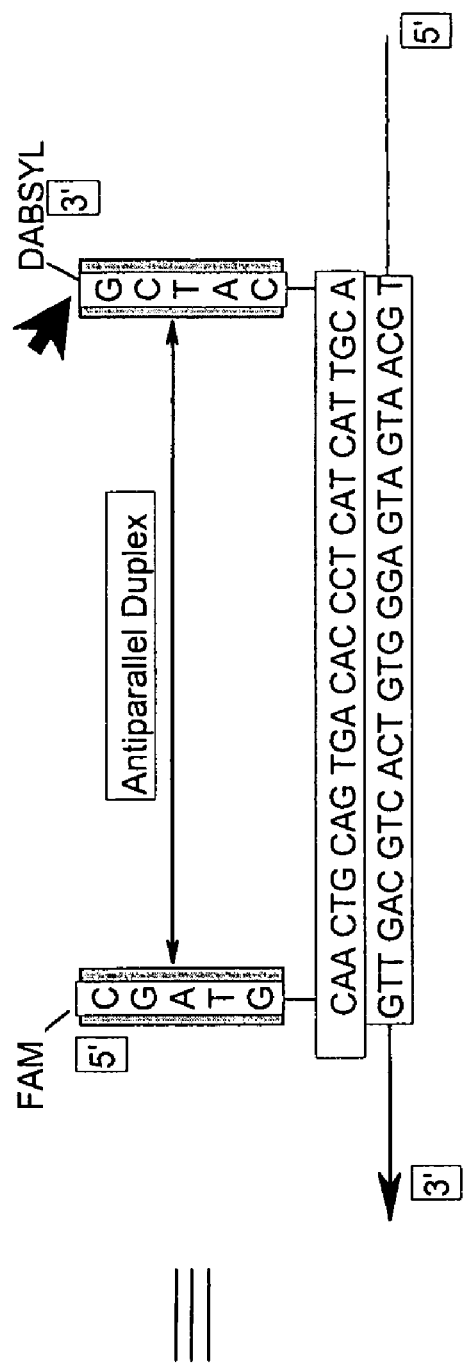
FIG. 1 shows an example of a labeled oligonucleotide according to the invention comprising a first segment and a third segment (stem) synthesized with alpha-nucleosides (shaded) and a second segment (loop) synthesized with beta-nucleosides, as described in Example 1A.

The following examples are given by way of illustration and are in no way limiting in nature. They will make it possible to understand the invention more clearly.

EXAMPLE 1

Process for Synthesizing the Oligonucleotides According to the Invention

Starting materials: The natural nucleotides which have been modified in 3' with a phosphoramidite group are called 3' beta-amidites. These oligonucleotides are commercially available and purchased from Glen Research (Foster City, USA).

The natural nucleotides, which have been modified in 5' with a phosphoramidite group are called 5' beta-amidites, they are also commercially available and purchased from Glen Research (Foster City, USA).

The alpha-anomeric nucleotides modified in 3' with a phosphoramidite group are called 3' alpha-amidites, they are commercially available and purchased from Chemgenes (Wilmington, USA).

The CPG dabsyl (Controled pore glass, CPG) and the 6-Fluorescein phosphoramidite are sold by Glen Research (Foster City, USA).

TABLE 1

| Molecules | Name | Ref. |
|---|---|---|
| 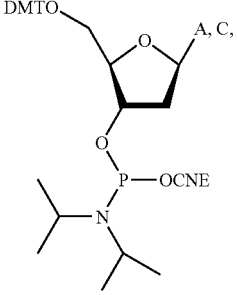 | 3' beta-amidites | Glen Research ref A, C, G and T: 10-1000-C2; 10-1010-C2; 10-1020-C2; 10-1030-C2 |
| 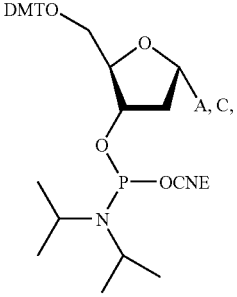 | 3' alpha-amidites | Chemgenes (A, C, G and T): ANP 1651; ANP 1652; ANP 1653; ANP 1654. |
| 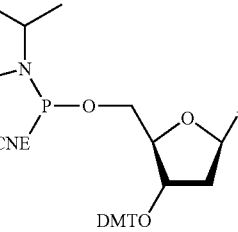 | 5' beta-amidites | Ref Glen (A, C, G and T): 10-0001-02; 10-0101-02; 10-0201-02; 10-0301-02 |

Oligonucleotide synthesis: 3' beta-amidites, 5' beta-amidites and 3' alpha-amidites were used for the oligonucleotide synthesis since the reactivity of said amidites is very similar. Preferably, a CPG dabsyl and 6-Fluorescein phosphoramidite were used. The phosphoramidite synthesis method has been described by Beaucage and Lyer (Tetrahedron, 48, 223-2311, 1992).

In general, the first nucleoside of the sequence to be synthesized is attached to a solid support (CPG) in the 3' position (or in 5'), the 5'OH (or 3') end of the nucleoside being protected with an acid-labile dimethoxytrityl (DMT) group.

In a first detritylation step, an acid treatment (tri- or dichloroacetic acid) made it possible to remove the DMT group in order to generate a reactive OH end.

In a second, coupling step, the phosphoramidite of the base to be added is condensed (in 5' or in 3') with this first elongation site in order to generate a phosphite triester bond. The condensation was carried out in the presence of a catalyst (tetrazole or S-thio ethyl tetrazole, or DCI, or etc.).

In a third, capping step, the —OH groups which have not reacted in the previous condensation step are blocked with an acylating reactant (acetic anhydride) in order to prevent deletions in the sequence.

In a fourth, oxidation step, the phosphite triester bond was oxidized to a phosphate triester bond using an oxidizing agent (aqueous iodine). The phosphite triester bond may also be oxidized with Beaucage reagent in solution in acetonitrile so as to give a phosphorothioate triester bond.

Steps 1 to 4 were repeated as many times as necessary depending on the length of the sequence to be synthesized.

When the desired sequence was finished, the solid support bearing the oligonucleotide was incubated in a concentrated aqueous solution of ammonia in order to cleave the oligonucleotide from the support, and to deprotect the bases and the phosphate groups.

The crude oligonucleotide thus obtained was precipitated from a solution of acetone and sodium perchlorate before being assayed at 260 nm (Spectramax, Molecular Device). 50 nmole of crude oligonucleotide was then purified on an XTerra C8 4.6×150 3.5 µm column, in a single step (Alliance HPLC system, WATERS), with a gradient of acetonitrile/TEAAc. The purest fractions were verified by ion exchange chromatography on a Gen Pack Fax column (Alliance HPLC system, WATERS) in a gradient of NaCl at pH 12.

The fractions were combined and evaporated and the mixture was then re-assayed and re-analyzed by HPLC before being used.

1A-First Embodiment of the Invention According to which Said First and Third Segments (Stem Part) of the Oligonucleotide Comprise Alpha-Phosphoramidites (FIG. 1)

An oligonucleotide comprising a second segment, or loop, in beta-anomeric configuration, and a stem in alpha-anomeric configuration (first and third segments) forming an antiparallel alpha/alpha duplex was used (oligonucleotide A). The synthesis of the oligonucleotide according to this first embodiment was initiated from the end comprising the dabsyl group (FIG. 1, see arrow). The loop was then synthesized with the beta-amidites, then the third segment was synthesized from alpha-amidites.

Figure 2:
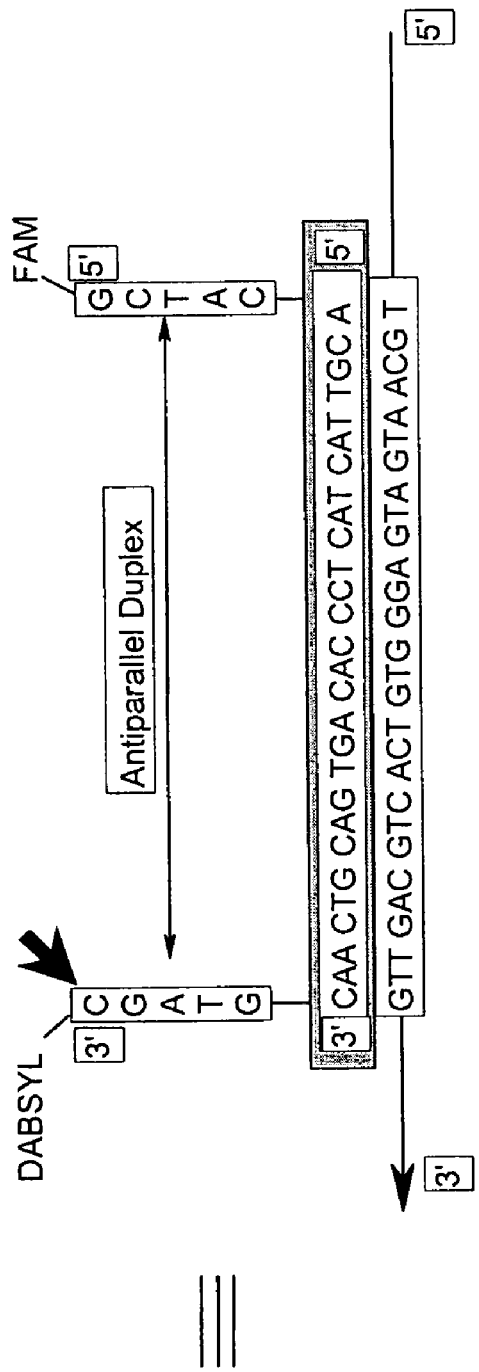
FIG. 2 shows an example of a labeled oligonucleotide according to the invention comprising a first segment and a third segment (stem) synthesized with beta-nucleosides and a second segment (loop) synthesized with alpha-nucleosides (shaded), as described in Example 1B.

1B-Second Embodiment of the Invention According to which Said Second Segment ("Loop" Part) of the Oligonucleotide Comprises Alpha-Phosphoramidites (FIG. 2)

Compared with the previous embodiment, the initial oligonucleotide in this case comprises a second segment (loop) comprising alpha-nucleotides which hybridize in parallel fashion with the target (oligonucleotide B).

The first and third segments (stem part) comprise beta-nucleotides. The synthesis began with beta-amidites and then the loop was synthesized with alpha-amidites before returning to the beta-amidites for the synthesis of the remaining stem (FIG. 2, see arrow).

1C-Third Embodiment of the Invention According to which Said First, Second And Third Segments ("Stem" And "Loop" Parts) of the Oligonucleotide Comprise Alpha-Phosphoramidites Compared with the previous embodiment, the initial oligonucleotide is in this case completely modified with alpha-nucleosides (loop and stem). The alpha-nucleotides of the loop hybridize in parallel fashion with the target, whereas those of the stem hybridize with one another in antiparallel fashion (oligonucleotide C).

Figure 3:
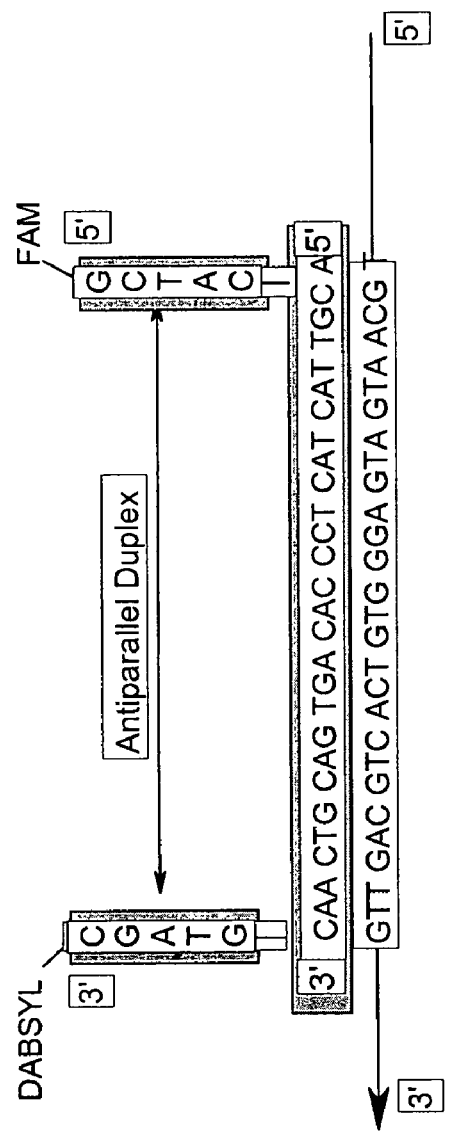
FIG. 3 shows an example of a labeled oligonucleotide according to the invention comprising a first segment and a third segment (stem), and also a second segment (loop) synthesized with alpha-nucleosides (shaded), as described in Example 1C.
Figure 3:
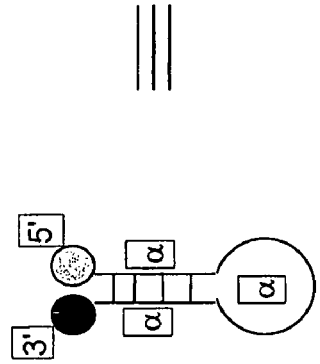
Figure 4:
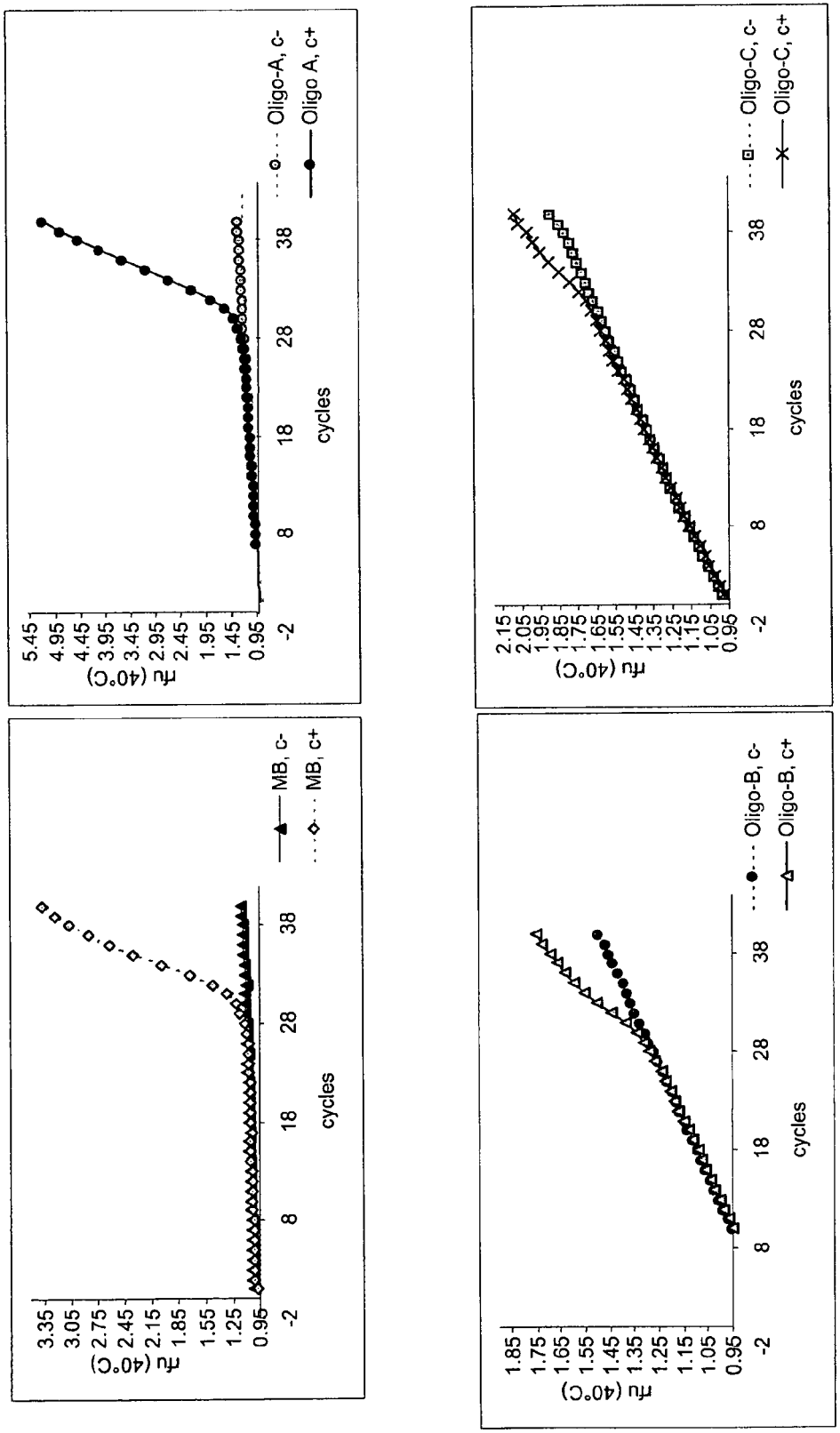
FIG. 4 shows the normalized fluorescence profiles, measured at 40° C., of the modified or unmodified molecular beacons as described in Example 2A.

The synthesis began and ended with alpha-amidites (FIG. 3).

EXAMPLE 2

Study of the Resistance of the Oligonucleotides According to the Invention to Cleavage by the 5'-Nuclease Activity of Taq Polymerase The objective of this experiment is to demonstrate that an oligonucleotide modified according to the invention (oligonucleotides A, B and C of Example 1) is not cleaved by the 5'-nuclease activity of Taq polymerase in an in vitro enzymatic amplification reaction.

Experimental design: The target sequence was the pCITE plasmid comprising a 1.2 Kb insert corresponding to a genetic sequence of the hMPV virus, at a concentration of $5 \cdot 10^3$ copies per tube.

The primers and probes used were the following:

SEQ ID No 1
Sense primer:
5'-CAT ATA AGC ATG CTA TAT TAA AAG AGT CTC-3'

SEQ ID No 2
Reverse primer:
5'-CCT ATT TCT GCA GCA TAT TTG TAA TCA G-3'

Modified probe according to the first embodiment of the invention (oligonucleotide A): SEQ ID No 3 5'-FAM-[GC TAC] CAA CTG CAG TGA CAC CCT CAT CAT TGCA [GTA GC]-Dabcyl-3'—The nucleotide sequences between square brackets, corresponding to the first and third "stem" segments, were composed of alpha-anomeric nucleotides. The beta-anomeric "loop" sequence underlined specifically recognized a sequence of the amplicon generated in the in vitro amplification. FAM is a fluorescein-type fluorophore, the fluorescence of which can be detected at 530 nm. Dabcyl is an aromatic molecule, which prevents the emission of fluorescence when it is physically in proximity to the FAM fluorophore.

Modified probe according to the second embodiment of the invention (oligonucleotide B): SEQ ID No 4 5'-FAM-GC TAC [ACGT TAC TAC TCC CAC AGT GAC GTC AAC] GTA GC-Dabcyl-3'—The nucleotide sequence between square brackets, corresponding to the second "loop" segment, was composed of alpha-anomeric nucleotides and specifically recognized a sequence of the amplicon generated in the in vitro amplification.

Modified probe according to the third embodiment of the invention (oligonucleotide C): SEQ ID No 5 5'-FAM-[GC TAC ACGT TAC TAC TCC CAC AGT GAC GTC AAC GTA GC]-Dabcyl-3'—The nucleotide sequence between square brackets, corresponding to the first, second and third segments, was composed of alpha-anomeric nucleotides. The sequence underlined, corresponding to the second "loop" segment, specifically recognized a sequence of the amplicon generated in the in vitro amplification.

Unmodified control probe (MB): SEQ ID No 6 5'-FAM-GC TAC CAA CTG CAG TGA CAC CCT CAT CAT TGCA GTA GC-Dabcyl-3'—This sequence, which is beta-anomeric, specifically recognized a sequence of the amplicon generated in the in vitro amplification.

PCR Amplification with Real Time Detection on a LightCycler:

A "LightCycler FastStart DNA Master Hybridization Probes" amplification kit (Roche, Penzberg, Germany) was used. The preparation of the reaction mixture was carried out according to the procedures recommended by the supplier. In a reaction volume of 20 µl, $5 \cdot 10^3$ copies of the plasmid were mixed with the sense and reverse primers (0.5 µM), the modified or unmodified nucleotide probe (1 µM) 2 µl of vial 1 of the kit (enzyme mix), 0.8 µl of 25 mM MgCl$_2$ of the kit and the PCR grade water of the kit. The reaction mixture was then introduced into a capillary tube, which was introduced into the LightCycler. For each amplification reaction, a control was carried out with the unmodified probe (MB) in place of the modified probe (oligonucleotide A, B or C). For each amplification reaction, a control was also carried out with the addition of PCR grade water from the kit, in place of the target plasmid (negative control, "c–").

The PCR reaction consisted of an initial denaturation of 8 minutes at 95° C., followed by 40 cycles at 95° C. for 30 seconds, 40° C. for 5 seconds and 60° C. for 60 seconds. The fluorescence was read at 530 nm, at a point at the end of each step in each cycle. The fluorescence results were then reprocessed on an Excel sheet so as to separate the results by temperature, to normalize them and to produce a graphic representation thereof. The graphs obtained for the readings at 40° C. and 60° C. served to verify the hybridization of the probe with the amplicons during the amplification reaction. At 95° C., on the other hand, no hybridization was possible between the probe and the amplicons. Any increase in signal at 95° C., compared with the negative control, could only be due to cleavage of the probe. The graph obtained for the reading at 95° C. therefore served to prove whether or not the probe had been cleaved by the 5'-nuclease activity of the TaqPol.

Figure 6:
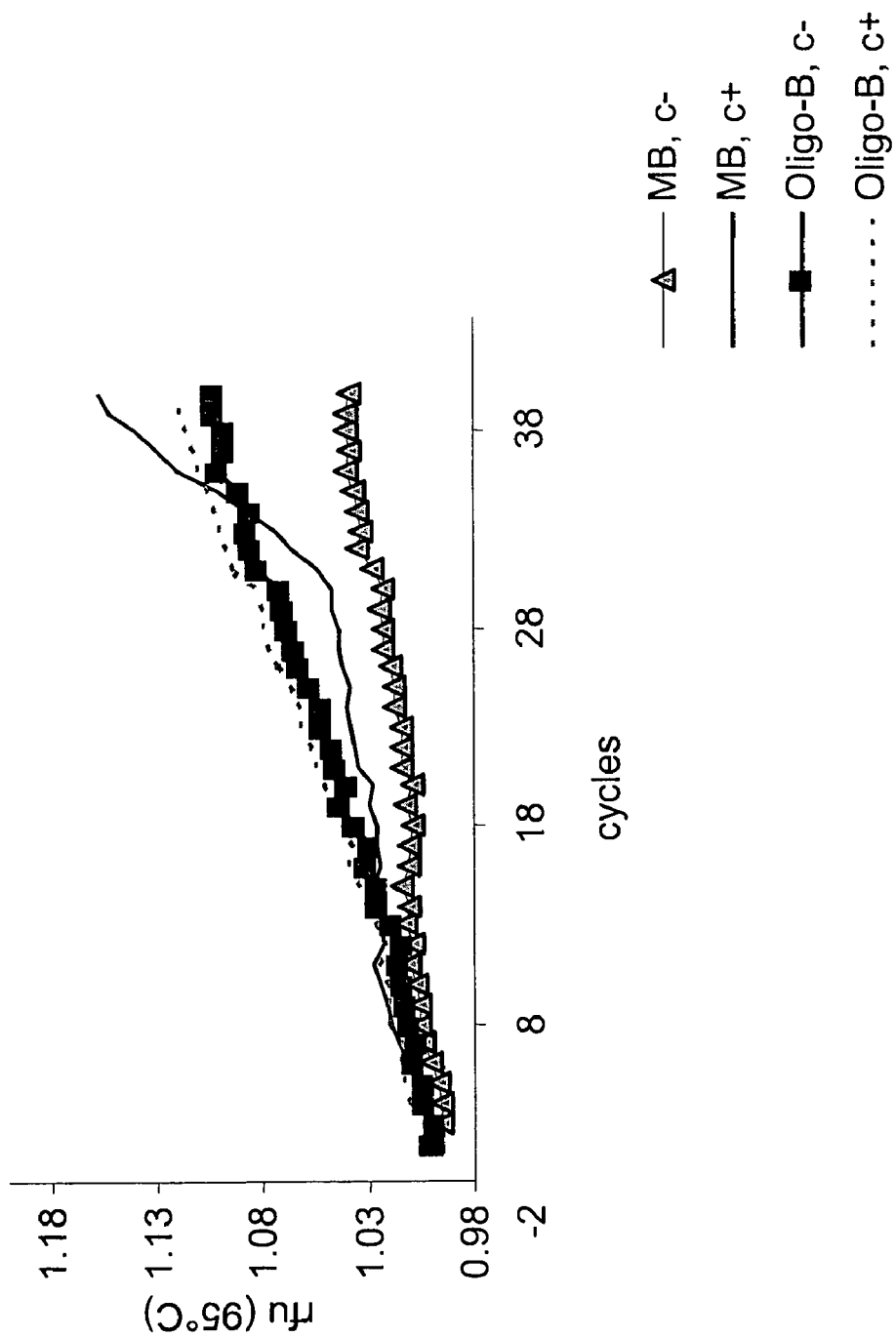
FIG. 6 shows the normalized fluorescence profiles, measured at 95° C., for the "Oligonucleotide B" and "MB" molecular beacons during the amplification on a Lightcycler, as described in Example 2A.

Results:

The profiles obtained in real time detection at 40° C. are shown in FIG. 6. The horizontal axis represents the number of amplification cycles, the vertical axis represents the fluorescence detected at 530 nm, at 40° C., in each cycle. Top left, "MB"; top right, "Oligonucleotide A"; bottom left, "Oligonucleotide B"; bottom right, "Oligonucleotide C". In each graph, the corresponding negative control is represented.

Figure 7:
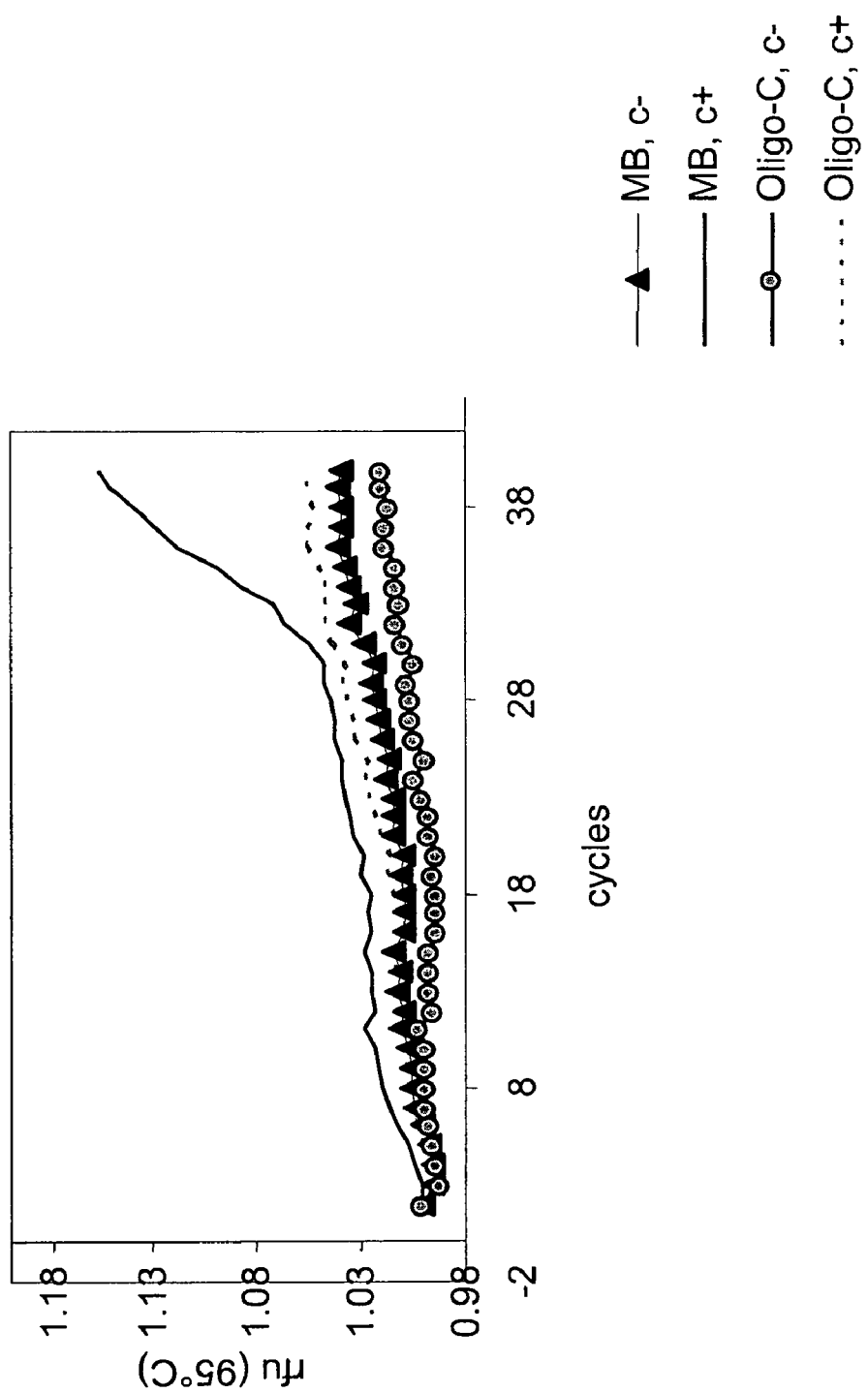
FIG. 7 shows the normalized fluorescence profiles, measured at 95° C., for the "Oligonucleotide C" and "MB" molecular beacons during the amplification on a Lightcycler, as described in Example 2A.
Figure 8:
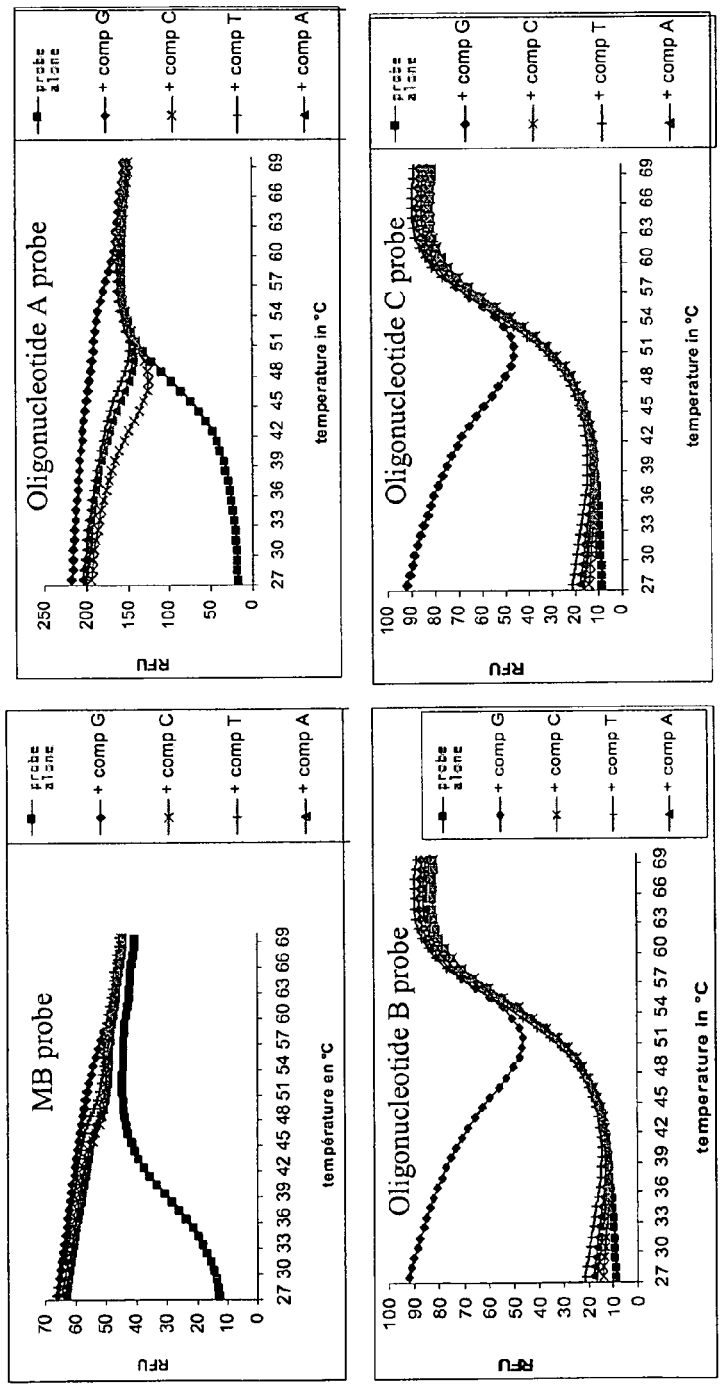
FIG. 8 shows the thermal denaturation profiles with measurement of the fluorescence for the probes studied with the various complementary sequences with or without mismatches, as described in Example 3.

The profiles obtained in real time detection at 95° C. are given in FIGS. 6 to 8. In each figure, the profile corresponding to one of the modified molecular beacons is represented, with, as control, the profile of the unmodified molecular beacon and that of the corresponding negative samples.

The result expected in the case of hybridization is an exponential increase in the fluorescence signal at 40° C. starting from the moment the number of amplicons increases. In the event of cleavage, an exponential increase in the fluorescence at 95° C., parallel to that observed for the hybridization, is expected. The linear increases or decreases in the signal do not correspond to any detection of the amplicon, since the latter is generated exponentially.

The profiles at 40° C. demonstrated that the modified nucleotide probes A, B and C and also the unmodified control MB specifically detected the presence of the amplicons derived from the in vitro enzymatic amplification reaction.

The profiles at 95° C. demonstrated that the MB and A probes were specifically cleaved during the amplification reaction, whereas the modified probes B and C were not cleaved under the same conditions.

Figure 5:
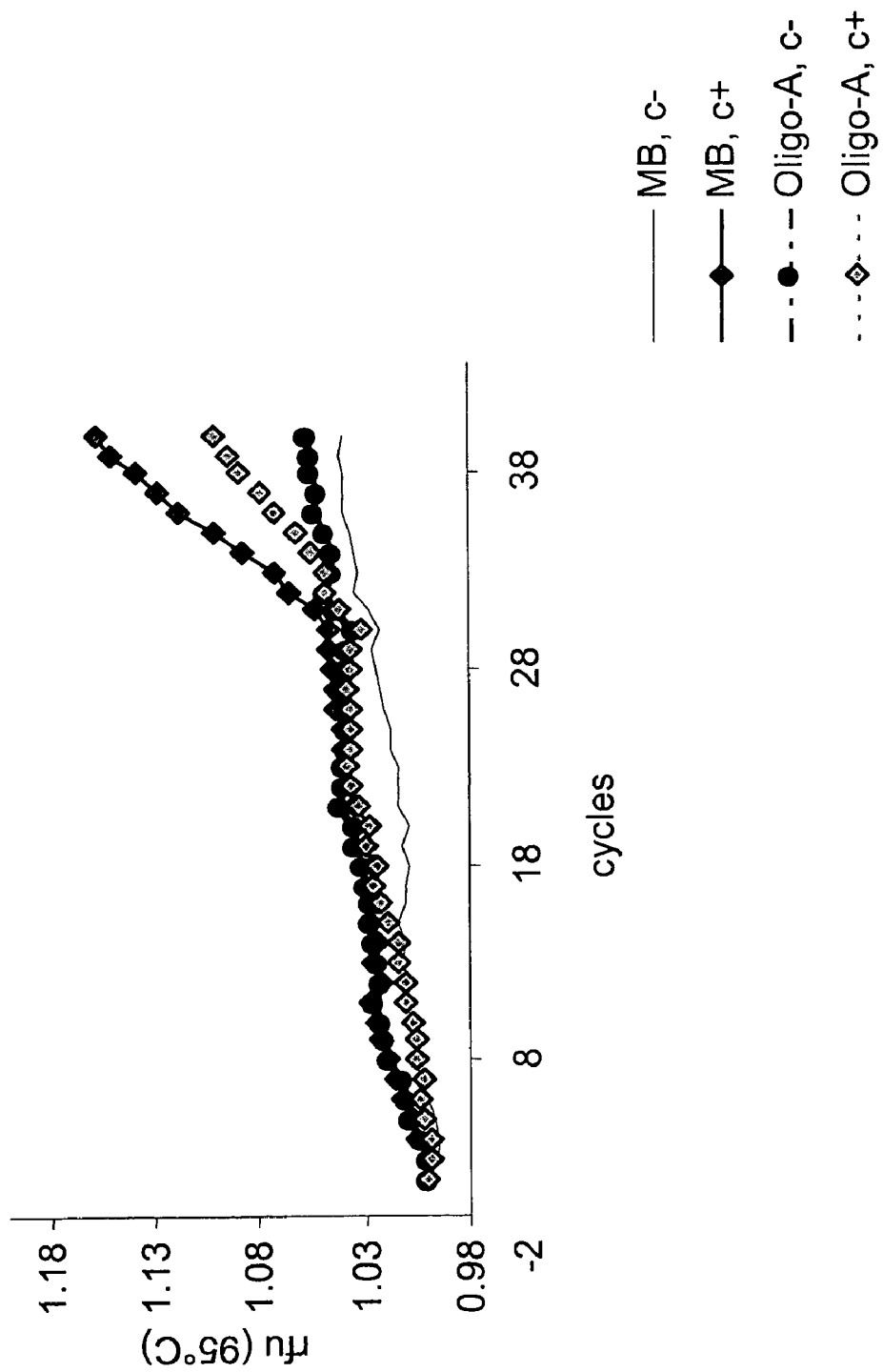
FIG. 5 shows the normalized fluorescence profiles, measured at 95° C., for the "Oligonucleotide A" and "MB" molecular beacons during the amplification on a Lightcycler, as described in Example 2A.

FIGS. 5 to 7 give the comparison of the increases in fluorescence at 95° C. for the unmodified "MB" probe and, respectively, for the modified probe "oligonucleotide A", "oligonucleotide B" and "oligonucleotide C". A specific increase in the fluorescence could be observed only for the MB probe and the "oligonucleotide A" probe, when the amplification takes place. When the amplification does not take place (negative controls, "c–") and when the second, "loop" segment of the nucleotide probe is modified (oligonucleotides B and C), there is no cleavage by the 5'-nuclease activity of Taq polymerase, and there is therefore no increase in fluorescence compared with the negative control.

Conclusion: The molecular beacons modified in the second, "loop" segment according to the invention (oligonucleotides B and C) hybridized specifically with the amplicons derived from the cycling on a lightcycler, giving rise to a real time detection comparable with that obtained with the unmodified molecular beacon "MB" and with the molecular beacon modified in the stem (oligonucleotide A). The molecular beacons modified in the loop were not cleaved by the 5'-nuclease activity of Taq polymerase, unlike the control molecular beacon "MB" and the molecular beacon modified in the stem, "oligonucleotide A".

EXAMPLE 3

Study of the Specificity of the Hybridization of the Oligonucleotides According to the Invention to their Target Sequence (FIG. 8)

Objective:

The aim of the experiment is to verify whether beacons comprising alpha-type nucleotides are more specific for their target than beacons composed only of beta-type nucleotides.

The specificity can be measured by calculating the difference in Tm (herein ΔTm) between a probe in solution with its completely complementary target and this probe in solution with a target comprising a nucleotide variation in its sequence (in this case, a mismatch). The ΔTms will be calculated for each probe and for each complementary sequence studied.

In our case, the specificity will be measured by the value of the ΔTms calculated with the oligonucleotide A, B and C probes and four complementary sequences, of which one is completely complementary to the second segment of the probes and the other three comprise a C, T or A mismatch relative to the completely complementary sequence.

Experimental Design

The sequences of the probes and of the complementary sequences used are described in Table 1 below.

The fluorescence of solutions containing the probes, in the presence of completely complementary target or target with a mismatch, was measured as a function of the temperature between 69 and 27° C. in an EasyQ thermoanalyzer spectrofluorimeter (bioMérieux bv, Boxtel, NL). All the measurements were carried out on solutions with a volume of 20 μL, at a probe concentration of 100 nM, and at the target concentration of 1 μM, in a buffered aqueous solution from the Nasba Basic kit (bioMérieux bv, Boxtel, NL).

TABLE 1

Sequences of the probes and complementary sequences used.

| SEQ ID | Names | Sequences |
|---|---|---|
| 9 | MB | fam-CGA TG-C AAC TGC AGT GAC ACC CTC ATC ATT GCA-CAT CG-dabsyl |
| 10 | Oligo A | fam-*CGA TG*-C AAC TGC AGT GAC ACC CTC ATC ATT GCA-*CAT CG*-dabsyl |
| 11 | Oligo B | fam-GCT AC-*ACG TTA CTA CTC CCA CAG TGA CGT CAA C* -GT AGC-dabsyl |
| 12 | Oligo C | fam-*GCT AC ACG TTA CTA CTC CCA CAG TGA CGT CAA C* -GT *ACG*-dabsyl |
| 13 | comp G | TT ATG ATG AGG GTG TCA CTG CAT T |
| 14 | comp C | TT ATG ATG AGG CTG TCA CTG CAT T |
| 15 | comp T | TT ATG ATG AGG TTG TCA CTG CAT T |
| 16 | comp A | TT ATG ATG AGG ATG TCA CTG CAT T |

In bold italics: alpha-nucleotides;
Underlined: mismatch.
All the sequences are written in the 5'-3' direction.

Results

The thermal denaturation profiles obtained are represented in FIG. 8. The Tm corresponds to the maximum of the first derivative of each profile. The Tm values obtained are indicated in Table 2 below.

TABLE 2

Tm of the various probes with the complementary sequences G, C, T and A.

| Tm in ° C. | MB | Oligo-nucleotide A | Oligo-nucleotide B | Oligo-nucleotide C |
|---|---|---|---|---|
| comp G | 56.9 | 56.4 | 44.3 | 42.3 |
| comp C | 44.9 (−12.0) | 41.8 (−14.6) | <30 | <30 |
| comp T | 47.7 (−9.2) | 45.4 (−11.0) | <30 | <30 |
| comp A | 46.6 (−10.3) | 43.9 (−12.5) | <30 | <30 |

Between brackets, values for ΔTm between the completely complementary sequence "comp G" and the other complementary sequences containing a mismatch.

In the case of the oligonucleotide A probe, the ΔTm values in Table 2 show a better specificity than the MB probe, around +2° C. Given that, in both cases, the complementary sequence is of beta type, this increase in specificity is certainly due to a greater stability of the hybridization of the stem (first and third complementary segments) in the case of the oligonucleotide A probe, which can be seen in FIG. 14.

In the case of the oligonucleotide B and C probes, the Tm values with the complementary sequences containing a mismatch could not be obtained since the hybridization was not sufficient in the temperature range used. This indicates a very high specificity, which can be verified in the thermal denaturation profiles in FIG. 8. It can be seen in these profiles that only the completely complementary sequence "comp G" hybridizes with these probes, while the complementary sequences containing a mismatch do not hybridize. Compared with the results obtained with the oligonucleotide A probe, these results show that the increase in specificity due to the hybridization of an alpha-type sequence is independent of the nature of the stem, which is of beta-type in the oligonucleotide B probe and of alpha-type in the oligonucleotide C probe.

Conclusion

The results show that the four modified probes have a higher specificity than the unmodified MB probe (Table 2). This increase in specificity is independent, in our case, of the nature of the stem (first and third complementary segments).

EXAMPLE 4

Study of the Hybridization of the Stem of a Molecular Beacon-Type Nucleic Probe with a Target Sequence Objectives When a molecular beacon-type nucleic probe hybridizes with its complementary target sequence, it is possible for the stem of the probe, both on the 5' side and on the 3' side, to also be able to hybridize with the target. This can produce an unforeseen increase in the stability of the hybridization and, consequently, a loss of specificity of the probe. The example described here serves to show that the combination of alpha- and beta-nucleotides in a molecular beacon-type nucleic probe makes it possible to avoid this problem by preventing the hybridization of the stem with the complementary target.

Experimental Design

The sequences of the probes used are the same as in Example 3, and are described in Table 1 above. The complementary sequences used are described in Table 3 below.

TABLE 3

Sequences of the complementary target oligonucleotides used.

| Names | Sequences |
|---|---|
| SEQ ID No18: comp+ | 5'-CGA TG T GCA ATG ATG AGG GTG TCA CTG CAT T |
| SEQ ID No19: comp− | 5'-GTA GC T GCA ATG ATG AGG GTG TCA CTG CAT T |

In bold, the sequence complementary to the loop of the probe.

The complementary sequences comprise a part on the 3' side which is complementary to the loop of the probe, and a part on the 5' side which is complementary, in the case of "comp+", or not complementary in the case of "comp−", to one side of the stem of the probe.

The fluorescence of solutions containing the various combinations of probes and of targets was measured as a function of the temperature between 69 and 27° C. in an EasyQ thermoanalyzer spectrofluorimeter (bioMérieux bv, Boxtel, NL). All the measurements were carried out on solutions with a volume of 20 µL, at a probe concentration of 100 nM and at the target concentration of 1 µM, in a buffered aqueous solution from the Nasba Basic kit (bioMérieux bv, Boxtel, NL).

Results

Figure 9:
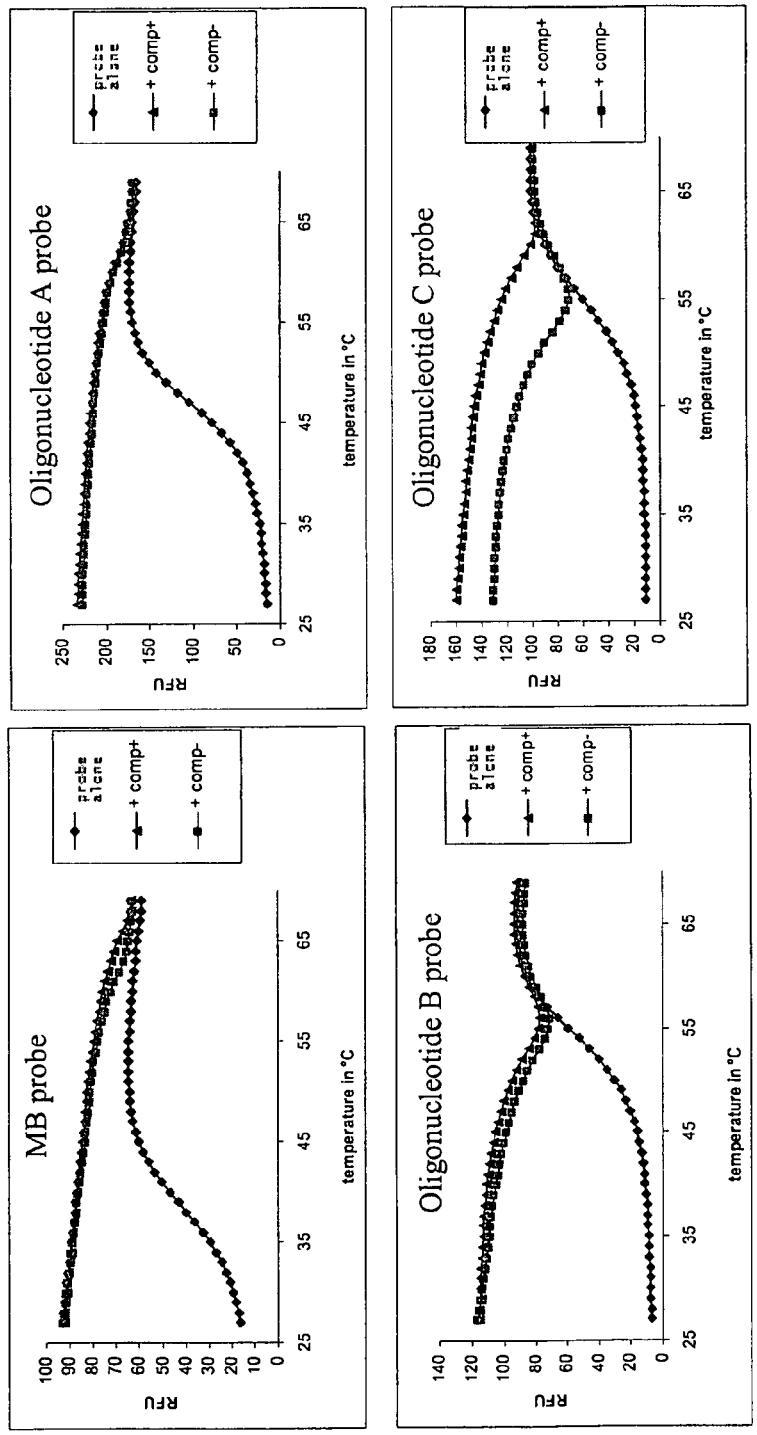
FIG. 9 shows the thermal denaturation profiles with measurement of the fluorescence for the probes studied with the targets complementary or not complementary to a part of the stem, as described in Example 4.

The thermal denaturation profiles obtained are represented in FIG. 9. The Tm corresponds to the maximum of the first derivative of each profile. The Tm values obtained are indicated in Table 4 below.

TABLE 4

Tm of the various probes with the comp+ and comp− complementary targets

| | probe | | | |
|---|---|---|---|---|
| target | MB | Oligonucleotide A | Oligonucleotide B | Oligonucleotide C |
| stem | 37.9 | 46.4 | 54.1 | 54.8 |
| comp+ | 64.4 | 60.9 | 51.5 | 57.2 |
| comp− | 60.5 | 60.7 | 51.0 | 50.6 |

A probe in which the loop is of beta-type will hybridize in the antiparallel orientation on a natural target sequence, necessarily of beta-type, such as those used here. A probe in which the loop is of alpha-type will hybridize in the parallel orientation on the same beta target sequences. As a result, depending on the nature of the loop, the stem will find itself opposite the sequence of the target in the orientation dictated by the hybridization of the loop. The alpha stem of a probe can therefore hybridize to the natural beta-target only if the latter is complementary (comp+) and if the loop of the probe is also alpha (parallel orientation). Similarly, the beta stem of a probe can hybridize to the natural beta-target only if the latter is complementary (comp+) and if the loop of the probe is also beta (antiparallel orientation). This implies that the stem of the MB and oligonucleotide C probes can hybridize with the complementary sequence of comp+, but not with the non-complementary sequence of comp−, causing a difference in Tm, which can be observed in Table 4. The stem of the oligonucleotide A and B probes cannot hybridize with the complementary sequence of comp+, nor with the noncomplementary sequence of comp−, and the Tm is similar with the two targets, as can be seen in Table 4.

Conclusion

The results show that the molecular beacon-type nucleic probes in which the nucleotides of the stem are anomerically different than the nucleotides of the loop (oligonucleotide A and B probes) prevent the hybridization of the stem with the complementary sequence present in the target, even when the complementarity is perfect. No negative effect on the hybridization is observed.

The invention claimed is:

1. A labeled oligonucleotide comprising a first nucleotide segment; a second nucleotide segment, complementary to a target sequence; a third nucleotide segment, complementary to said first nucleotide segment; a fluorophore; and a quencher, wherein:
   (1) said second segment comprises at least five alpha-anomeric nucleosides, and said first and third segments do not comprise an alpha-anomeric nucleoside; or
   (2) said second segment does not comprise an alpha-anomeric nucleoside, and said first and third segments each comprise at least one alpha-anomeric nucleoside.

2. The labeled oligonucleotide as claimed in claim 1, wherein said first and third segments are on either side of the second segment.

3. The labeled oligonucleotide as claimed in claim 1, wherein the fluorophore is at one end of said oligonucleotide and the quencher is at the other end of said oligonucleotide.

4. The labeled oligonucleotide as claimed in claim 1, wherein said fluorophore is fluorescein.

5. The labeled oligonucleotide as claimed in claim 1, wherein said quencher is dabsyl.

6. The labeled oligonucleotide as claimed in claim 1, wherein said first segment consists of from 3 to 8 nucleotides, said second segment consists of from 10 to 35 nucleotides, and said third segment consists of from 3 to 8 nucleotides.

7. A method for blocking nuclease activity, the method comprising:
   providing an oligonucleotide comprising at least one alpha-anomeric nucleoside and at least one beta-anomeric nucleoside in a reaction medium comprising at least one of a polymerase enzyme having 5'-nuclease activity and an enzyme having RNAse H activity; and
   blocking at least one of the 5'-nuclease activity and the RNAse H activity.

8. A process for detecting a nucleic material in a biological sample, comprising the following steps:
   a) extracting the nucleic material from a biological sample,
   b) amplifying the nucleic material in order to obtain amplicons of at least one target sequence of the nucleic material,
   c) using at least one labeled oligonucleotide simultaneously with step b) or subsequent to step b), and
   d) detecting the presence of said amplicons wherein said labeled oligonucleotide comprises a first nucleotide segment, a second nucleotide segment that is complementary to a target sequence, a third nucleotide segment that is complementary to said first nucleotide segment, a fluorophore, and a quencher,
wherein:
   said second segment comprises at least five alpha-anomeric nucleosides, and said first and third segments do not comprise an alpha-anomeric nucleoside; or
   said second segment does not comprise an alpha-anomeric nucleoside, and said first and third segments each comprise at least one alpha-anomeric nucleoside.

9. The labeled oligonucleotide as claimed in claim 1, wherein said second segment comprises at least five alpha-anomeric; nucleosides, and said first and third segments do not comprise an alpha-anomeric nucleoside.

10. The labeled oligonucleotide as claimed in claim 1, wherein said second segment does not comprise an alpha-anomeric nucleoside, and said first and third segments each comprise at least one alpha-anomeric nucleoside.

11. The labeled oligonucleotide as claimed in claim 1, wherein said second segment consists of alpha-anomeric nucleotides, and said first and third segments consist of beta-anomeric nucleotides.

12. The process as claimed in claim 8, wherein said second segment comprises at least one alpha-anomeric nucleoside, and said first and third segments do not comprise an alpha-anomeric nucleoside.

13. The process as claimed in claim 8, wherein said second segment does not comprise an alpha-anomeric nucleoside, and said first and third segments each comprise at least one alpha-anomeric nucleoside.

14. The process as claimed in claim 8, wherein said second segment consists of alpha-anomeric nucleotides, and said first and third segments consist of beta-anomeric nucleotides.

15. The labeled oligonucleotide as claimed in claim 1, wherein said second segment comprises at least ten alpha-anomeric nucleosides, and said first and third segments do not comprise an alpha-anomeric nucleoside.

16. The labeled oligonucleotide as claimed in claim 1, wherein said second segment comprises at least fifteen alpha-anomeric nucleosides, and said first and third segments do not comprise an alpha-anomeric nucleoside.

17. The process as claimed in claim 8, wherein said second segment comprises at least five alpha-anomeric nucleosides, and said first and third segments do not comprise an alpha-anomeric nucleoside.

18. The process as claimed in claim 8, wherein said second segment comprises at least ten alpha-anomeric nucleosides, and said first and third segments do not comprise an alpha-anomeric nucleoside.

19. The process as claimed in claim 8, wherein said second segment comprises at least fifteen alpha-anomeric nucleosides, and said first and third segments do not comprise an alpha-anomeric nucleoside.

* * * * *

SEQUENCE LISTING

<160> NUMBER OF SEQ ID NOS: 18

<210> SEQ ID NO 1
<211> LENGTH: 30
<212> TYPE: DNA
<213> ORGANISM: Human metapneumovirus

<400> SEQUENCE: 1
catataagca tgctatatta aaagagtctc                                                30

<210> SEQ ID NO 2
<211> LENGTH: 28
<212> TYPE: DNA
<213> ORGANISM: Human metapneumovirus

<400> SEQUENCE: 2
cctatttctg cagcatattt gtaatcag                                                  28

<210> SEQ ID NO 3
<211> LENGTH: 38
<212> TYPE: DNA
<213> ORGANISM: Human metapneumovirus

<400> SEQUENCE: 3
gctaccaact gcagtgacac cctcatcatt gcagtagc                                       38

<210> SEQ ID NO 4
<211> LENGTH: 38
<212> TYPE: DNA
<213> ORGANISM: Human metapneumovirus

<400> SEQUENCE: 4
gctacacgtt actactccca cagtgacgtc aacgtagc                                       38

<210> SEQ ID NO 5
<211> LENGTH: 38
<212> TYPE: DNA
<213> ORGANISM: Human metapneumovirus

<400> SEQUENCE: 5
gctacacgtt actactccca cagtgacgtc aacgtagc                                       38

<210> SEQ ID NO 6
<211> LENGTH: 38
<212> TYPE: DNA
<213> ORGANISM: Human metapneumovirus

<400> SEQUENCE: 6
gctaccaact gcagtgacac cctcatcatt gcagtagc                                       38

<210> SEQ ID NO 7
<211> LENGTH: 33
<212> TYPE: DNA
<213> ORGANISM: Human metapneumovirus

<400> SEQUENCE: 7
acgttactac tcccacagtg acgtcaacgt agc                                            33

<210> SEQ ID NO 8
<211> LENGTH: 27
<212> TYPE: DNA
<213> ORGANISM: Human metapneumovirus

```
<400> SEQUENCE: 8
tgcaatgatg agggtgtcac tgcggtt                                    27

<210> SEQ ID NO 9
<211> LENGTH: 38
<212> TYPE: DNA
<213> ORGANISM: Human metapneumovirus

<400> SEQUENCE: 9
cgatgcaact gcagtgacac cctcatcatt gcacatcg                        38

<210> SEQ ID NO 10
<211> LENGTH: 38
<212> TYPE: DNA
<213> ORGANISM: Human metapneumovirus

<400> SEQUENCE: 10
cgatgcaact gcagtgacac cctcatcatt gcacatcg                        38

<210> SEQ ID NO 11
<211> LENGTH: 38
<212> TYPE: DNA
<213> ORGANISM: Human metapneumovirus

<400> SEQUENCE: 11
gctacacgtt actactccca cagtgacgtc aacgtagc                        38

<210> SEQ ID NO 12
<211> LENGTH: 38
<212> TYPE: DNA
<213> ORGANISM: Human metapneumovirus

<400> SEQUENCE: 12
gctacacgtt actactccca cagtgacgtc aacgtacg                        38

<210> SEQ ID NO 13
<211> LENGTH: 24
<212> TYPE: DNA
<213> ORGANISM: Human metapneumovirus

<400> SEQUENCE: 13
ttatgatgag ggtgtcactg catt                                       24

<210> SEQ ID NO 14
<211> LENGTH: 24
<212> TYPE: DNA
<213> ORGANISM: Human metapneumovirus

<400> SEQUENCE: 14
ttatgatgag gctgtcactg catt                                       24

<210> SEQ ID NO 15
<211> LENGTH: 24
<212> TYPE: DNA
<213> ORGANISM: Human metapneumovirus

<400> SEQUENCE: 15
ttatgatgag gttgtcactg catt                                       24

<210> SEQ ID NO 16
<211> LENGTH: 24
<212> TYPE: DNA
<213> ORGANISM: Human metapneumovirus
```

```
<400> SEQUENCE: 16
ttatgatgag gatgtcactg catt                                          24

<210> SEQ ID NO 17
<211> LENGTH: 31
<212> TYPE: DNA
<213> ORGANISM: Human metapneumovirus

<400> SEQUENCE: 17
cgatgtgcaa tgatgagggt gtcactgcat t                                  31

<210> SEQ ID NO 18
<211> LENGTH: 31
<212> TYPE: DNA
<213> ORGANISM: Human metapneumovirus

<400> SEQUENCE: 18
gtagctgcaa tgatgagggt gtcactgcat t                                  31
```